(12) United States Patent
Fomina et al.

(10) Patent No.:     US 12,590,957 B2
(45) Date of Patent:     *Mar. 31, 2026

(54) METHODS FOR MEASURING AN AMOUNT OF AN ANALYTE IN A COMPLEX SAMPLE

(71) Applicant: Robert Bosch GmbH, Stuttgart (DE)

(72) Inventors: Nadezda Fomina, Redwood City, CA (US); Christopher Johnson, San Carlos, CA (US); Young Shik Shin, Mountain View, CA (US); Christoph Lang, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/678,144

(22) Filed: May 30, 2024

(65)          Prior Publication Data

US 2024/0319183 A1     Sep. 26, 2024

Related U.S. Application Data

(63) Continuation of application No. 16/881,489, filed on May 22, 2020, now abandoned.

(51) Int. Cl.
G01N 33/544          (2006.01)
G01N 27/327          (2006.01)
G01N 33/84          (2006.01)

(52) U.S. Cl.
CPC ....... G01N 33/544 (2013.01); G01N 27/3277 (2013.01); G01N 33/84 (2013.01)

(58) Field of Classification Search
None
See application file for complete search history.

(56)          References Cited

U.S. PATENT DOCUMENTS

| | | | |
|---|---|---|---|
| 9,766,197 B2 * | 9/2017 | Johnson | ............. G01N 27/3272 |
| 9,797,894 B2 | 10/2017 | Kumar et al. | |
| 9,810,688 B2 * | 11/2017 | Fomina | ............. G01N 27/3272 |

(Continued)

OTHER PUBLICATIONS

Jones et al. A substrate amplification system for enzyme-linked immunoassays. II. Demonstration of its applicability for measuring anti-DNA antibodies. J Immunol Methods. Mar. 10, 1989;118(1):79-84. (Year: 1989).*

(Continued)

*Primary Examiner* — Rebecca M Giere
*Assistant Examiner* — Alexander Alexandrovic Volkov
(74) *Attorney, Agent, or Firm* — Brooks Kushman P.C.

(57)          ABSTRACT

A method for detecting an amount of an analyte in a solution includes providing an assay chamber including an electrode positioned at a first end of the assay chamber and a capture molecule attached to the electrode via a linker. A solution including an analyte, a binding partner of the analyte, at least one electrochemically active agent, and a detecting probe having a signaling tag attached thereto may be provided to the assay chamber. An electrical signal may be applied to the electrode to change the pH of the solution in the area near the electrode. The analyte may bind to the capture molecule and to the detecting probe at the first end of the assay chamber at the new pH. A signal produced by the signaling tag at the first end of the assay chamber may be measured to calculate the amount of the analyte in the solution.

20 Claims, 7 Drawing Sheets

(56) References Cited

U.S. PATENT DOCUMENTS

| | | |
|---|---|---|
| 9,910,008 B2 | 3/2018 | Johnson et al. |
| 10,379,080 B2 | 8/2019 | Johnson et al. |

OTHER PUBLICATIONS

Nguyen et al. Protection of immunoreactivity of dry immobilized proteins on microtitration plates in ELISA: application for detection of autoantibodies in myasthenia gravis. J Biotechnol., 1999, vol. 72, pp. 115-125. (Year: 1999).*

Li et al. Immunoassays for aflatoxins, Trends in Analytical Chemistry, 2009, vol. 28, pp. 1115-1126. (Year: 2009).*

Partridge et al. Minimizing target interference in PK immunoassays: new approaches for low-pH-sample treatment. Bioanalysis. Aug. 2013;5(15):1897-910. (Year: 2013).*

Doucet et al. Development and validation of an ELISA at acidic pH for the quantitative determination of IL-13 in human plasma and serum. Dis Markers. 2013;35(5):465-74. (Year: 2013).*

Bloem et al. Immunogenicity of Therapeutic Antibodies: Monitoring Antidrug Antibodies in a Clinical Context. Ther Drug Monit. Aug. 2017;39(4):327-332. (Year: 2017).*

Chazotte, B. et al., "Labeling Golgi with Fluorescent Ceramides," Cold Spring Harbor Protocols, Year: 2012, pp. 913-915, DOI: 10.1101/pdb.prot070599.

Du, L. et al., "Piezoelectric olfactory receptor biosensor prepared by aptamer-assisted immobilization," Sensors and Actuators B: Chemical, Year: 2013, vol. 187, pp. 481-487, DOI: 10.1016/j.snb.2013. 02.009.

Fomina et al., "An electrochemical platform for localized pH control on demand", Article from Royal Society of Chemisty, Lab Chip, 2016, 16, 2236-2244, May 20, 2016, 9 pages.

Konig, T et al., "Use of an albumin-binding domain for the selective immobilisation of recombinant capture antibody fragments on ELISA plates," Journal Immunological Methods, Year: 1998, vol. 218, pp. 73-83.

Lorenson, M. Y., et al., "Enzyme-linked oligonucleotide hybridization assay for direct oligo measurement in blood," Biology Methods and Protocols, Year: 2019, vol. 4, pp. 1-8, DOI: 10.1093/biomethods/ bpy014.

Sigma, "Alkaline Phosphatase—Assays, Molecular Weight, Substrates, and Structure," Year: 2023, 6 pages, https://www.sigmaaldrich. com/US/en/technical-documents/technical-article/protein-biology/ western-blotting/alkaline-phosphatase.

Wikipedia, "ELISA," Year: 2024, 9 pages, https://en.wikipedia.org/ w/index.php?title=ELISA&oldid=1195317246.

* cited by examiner

METHODS FOR MEASURING AN AMOUNT OF AN ANALYTE IN A COMPLEX SAMPLE

CROSS-REFERENCE TO RELATED APPLICATIONS

This application is a continuation of U.S. patent application Ser. No. 16/881,489, filed May 22, 2020, which is hereby incorporated by reference in its entirety.

TECHNICAL FIELD

The present disclosure relates to methods for measuring an amount of an analyte in a complex sample, for example, methods for measuring an amount of an analyte in an immunogenicity assay.

BACKGROUND

Suboptimal performance of protein assays is often due to sample complexity and non-specific interactions, especially for some immunogenicity assays and cytokine assays. For example, in an immunogenicity assay, drugs can bind to anti-drug antibodies (ADA), thereby forming drug-ADA complexes which can adversely affect an accurate quantification of the concentration of the ADA or the drug. In addition, cytokines and protein biomarkers often have native binding partners in blood and serum, and complexes can also be formed in an assay to affect an accurate detection of a target analyte. A pH treatment step can be performed to break up such complexes and other undesired interactions prior to assaying a sample. However, this step is often performed manually, which is not ideal for accurately measuring the concentration of a target analyte in the sample.

SUMMARY

According to an embodiment, a method for detecting an amount of an analyte in a solution is disclosed. The method may include providing an assay chamber including an electrode positioned at a first end of the assay chamber and a capture molecule attached to the electrode via a linker. The method may also include providing to the assay chamber a solution including an analyte, a binding partner of the analyte, at least one electrochemically active agent, and a detecting probe having a signaling tag attached thereto. The solution may be in contact with the electrode and may have a first pH value at which the signaling tag is in an off state. The method may also include applying a first electrical signal to the electrode to change the pH of the solution at the first end of the assay chamber from the first pH value to a second pH value. The pH of the solution at the end opposite the first end of the assay chamber may remain at the first pH value. The method may also include binding the analyte to the capture molecule and to the detecting probe at the first end of the assay chamber and measuring a signal produced by the signaling tag at the second pH value.

According to another embodiment, a method for detecting an amount of an analyte in a solution is disclosed. The method may include providing an assay chamber including an electrode positioned at a first end of the assay chamber and a capture molecule attached to the electrode via a linker. The method may also include providing to the assay chamber a solution including an analyte, a binding partner of the analyte, at least one electrochemically active agent, and a detecting probe having a signaling tag attached thereto. The solution may be in contact with the electrode and may have a first pH value at which the signaling tag is in an off state. The method may also include applying a first electrical signal to the electrode to change the pH of the solution at the first end of the assay chamber from the first pH value to a second pH value. The pH of the solution at the end opposite the first end of the assay chamber may remain at the first pH value. The method may also include binding the analyte to the capture molecule and to the detecting probe at the first end of the assay chamber and applying a second electrical signal to the electrode to change the pH of the solution at the first end of the assay chamber from the second pH value to a third pH value. The pH of the solution at the end opposite the first end of the assay chamber may remain at the first pH value, and the signaling tag may produce a second signal at the third pH value. The method may also include measuring the second signal produced by the signaling tag at the third pH value.

According to yet another embodiment, a method for detecting an amount of an analyte in a solution is disclosed. The method may include providing an assay chamber including an electrode positioned at a first end of the assay chamber and a capture molecule attached to the electrode via a linker. The method may also include providing to the assay chamber a solution including an analyte, a binding partner of the analyte, at least one electrochemically active agent, and a detecting probe having a signaling tag attached thereto. The solution may be in contact with the electrode and may have a first pH value at which the signaling tag is in an off state. The method may also include applying a first electrical signal to the electrode to change the pH of the solution at the first end of the assay chamber from the first pH value to a second pH value. The pH of the solution at the end opposite the first end of the assay chamber may remain at the first pH value. The method may also include dissociating the binding partner of the analyte from the analyte at the first end of the assay chamber at the second pH value, then applying a second electrical signal to the electrode to change the pH of the solution at the first end of the assay chamber from the second pH value to the first pH value. The pH of the solution at the first end of the assay chamber and at the end opposite the first end of the assay chamber may be at the first pH value. The method may also include binding the analyte to the capture molecule and to the detecting probe at the first end of the assay chamber then applying a third electrical signal to the electrode to change the pH of the solution at the first end of the assay chamber from the first pH value to the second pH value. The pH of the solution at the end opposite the first end of the assay chamber may remain at the first pH value. The method may also include dissociating the binding partner of the analyte from the analyte at the first end of the assay chamber at the second pH value then applying a fourth electrical signal to the electrode to change the pH of the solution at the first end of the assay chamber from the second pH value to the first pH value. The pH of the solution at the first end of the assay chamber and at the end opposite the first end of the assay chamber may be at the first pH value. The method may also include binding the analyte to the capture molecule and to the detecting probe at the first end of the assay chamber then applying a next electrical signal to the electrode to change the pH of the solution at the first end of the assay chamber from the second pH value to a third pH value. The signaling tag may be in an on state at the third pH value. The method may also include measuring a signal produced by the signaling tag at the third pH value.

DETAILED DESCRIPTION

Figure 1:
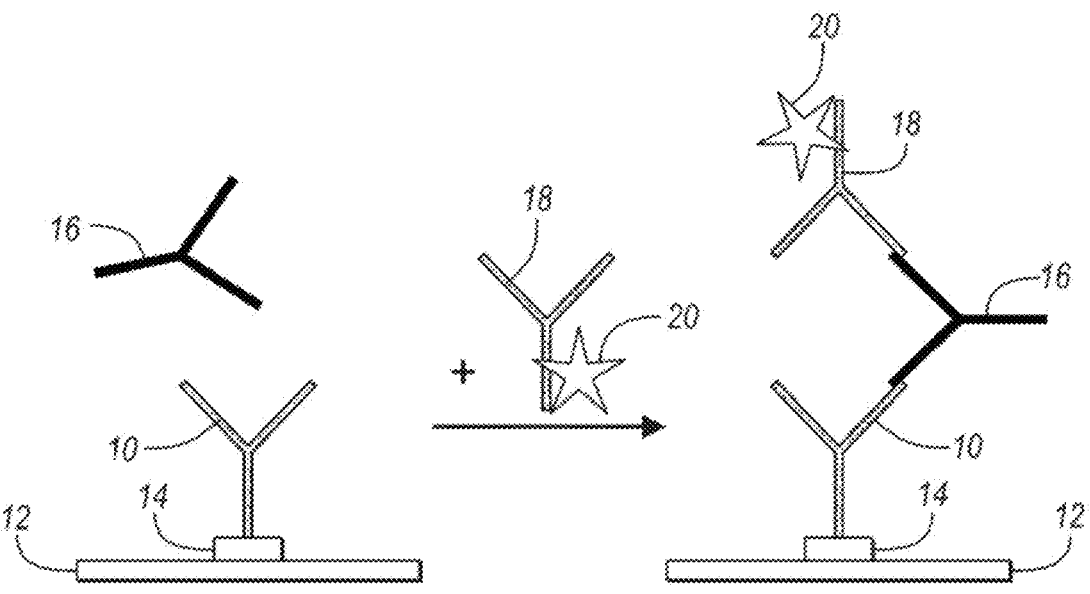
FIG. 1 depicts a schematic diagram of a method for detecting an amount of an analyte in an assay.

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This present disclosure is not limited to the specific embodiments and methods described below, as specific components and/or conditions may, of course, vary. Furthermore, the terminology used herein is used only for the purpose of describing embodiments of the present disclosure and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

Reference is being made in detail to compositions, embodiments, and methods of embodiments known to the inventors. The disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure.

Biotherapeutics, such as proteins and monoclonal antibodies (mAbs), are growing fast on the pharmaceutical market. Currently, over 250 approved biotherapeutics are on the market, and more than 500 are under development. Biotherapeutics, compared to relatively small molecule drugs, are prone to the risk of immune responses. For example, an unwanted immunogenicity may lead to a production of anti-drug antibodies (ADAs), which can negatively impact drug levels in circulation and drug efficacy. In some cases, immune responses can be severe and life threatening. Therefore, to assess the risk of immune responses against biotherapeutics, pharmacokinetics (PK) and pharmacodynamics (PD) characterizations are necessary during pre-clinical development stages and clinical trials.

To characterize PK and/or PD profiles for a biotherapeutic, it is important to accurately measure the concentration of ADAs, drugs, or both in an aqueous environment. However, high drug levels in the aqueous environment can adversely interfere with the detection of ADAs, especially in bridging assay formats. For example, in an immunogenicity assay, ADAs can form complexes with drugs in a sample solution, thereby preventing an accurate quantification of the concentration of the ADAs, the drugs, or both. Such an issue may be more common in multiple-dose studies, where drug concentrations remain high for a significant period of the studies.

To overcome the issue, drug-tolerant assays have been developed. The drug-tolerant assays can measure the concentration of ADAs in the presence of drugs by adopting an acid treatment step. The acid treatment step can break up ADA-drug complexes and release ADAs and drugs to a sample solution. Some examples of the drug-tolerant assays include enzyme-linked immunosorbent assay (ELISA), affinity capture elution ELISA (ACE), biotin-drug extraction with acid dissociation (BEAD) assay, sample pretreatment bridging ELISA, acid dissociation radioimmunoassay, homogeneous mobility shift assay (HMSA), and precipitation and acid dissociation method.

Besides ADAs, soluble drug targets may also present a challenge for immunoassays. When the ratio of drugs to drug targets is low, very few binding sites of the drugs are available to engage the drug targets that are immobilized in an immunoassay. However, when the ratio of drugs to drug targets are high, a reverse effect may be observed (i.e. very few binding sites of the drug targets are available to bind the drugs). Therefore, different ratios of drugs to drug targets in an immunoassay may also have an impact on the accuracy of measuring the PK and/or PD profiles for a biotherapeutic.

To resolve the problem, an acid treatment step has been employed in performing an immunoassay. The acid treatment step may be conducted by modulating a pH of a sample solution, thereby dissociating drugs from drug targets and denaturing drug-binding epitopes on drug targets. The sample solution may then be neutralized and ready for analysis in an ELISA format. This method has been used for the detection of immunoglobulin G1 (IgG1) mAb in the presence of angiopoietin-2 (Ang2).

Similarly, a sample may be subject to a mild acid treatment, followed by a direct analysis on the sample using a sandwich ELISA. This method does not denature drug-binding epitopes on drug targets, but it utilizes the ability of capture antibodies to bind to drugs at a specific pH value where the drugs and the drug targets remain dissociated (i.e. drugs are unbound to drug targets). This method has been applied to the detection of immunoglobulin G4 (IgG4) in the presence of a soluble circulating target.

Further, an improved assay conducted in an acidic pH value has been utilized for the detection of interleukin 13 (IL-13) in human plasma and serum. Specifically, incubation of a sample at the acidic pH value can reduce non-specific binding and interference from IL-13 binding proteins. Examples of biomarkers known to have soluble binding partners in blood and serum are, but not limited to, interleukin 1 (IL-1), interleukin 18 (IL-18), insulin-like growth factor 1 (IGF-1), tumor necrosis factor-beta (TNF-$\beta$), and testosterone.

To perform a bridging ELISA protocol, a sample solution may be diluted in acetic acid and then incubated for 1 hour. Thereafter, the solution may be mixed with a basic buffer (e.g. Tris pH 9.5) and then added to an assay plate which contains a surface-bound capture molecule (e.g. antigen). The solution may then be incubated for another 1 to 5 hours, followed by washing and signal amplification steps (e.g. using horseradish peroxidase, or alkaline phosphatase).

In view of the foregoing, the acid treatment step introduced in each method is performed manually. Manual operations can unavoidably introduce human errors, causing a low reproducibility of an assay. Therefore, there is a need to detect an amount of an analyte, such as an ADA, in an immunoassay in a more efficient and accurate manner.

In contrast to manually adjusting a pH of a sample solution, the pH of the sample solution may be modulated automatically. Methods of electrochemically modulating a pH of a sample solution, especially varying the pH of the sample solution near an electrode surface, have been disclosed in U.S. patent application Ser. Nos. 14/792,569 and 13/543,300, which are hereby incorporated by reference in their entirety. Generally, modulating pH electrochemically can give advantages toward performing an assay, including reducing the number of manual steps and reagents, shortening assay times, allowing multiplexing, and improving measurement accuracy. A system for electrochemically modulating a pH of a sample solution may include a working electrode and a counter electrode. The system may also include an electrochemically active agent, such as quinone, which may be added to the sample solution. The electrochemically active agent may undergo an electrochemical redox reaction (i.e. oxidation or reduction) under the influence of an electrical current. The electrochemical redox reaction of the electrochemically active agent may generate or consume hydrogen ($H^+$) ions, causing a pH change in the sample solution. By controlling the electrical current applied to the working electrode, only the sample solution near a surface of the working electrode may undergo the pH change while the pH of other areas of the sample solution that are not near the surface of the working electrode may not be affected. In addition, the system may also include a reference electrode and a sensing electrode. The sensing electrode may actively measure the pH of the sample solution in real time. Signals generated from the sensing electrode may be transmitted to electronics and fed into a closed loop algorithm, which may be used to control the electrical current applied to the working electrode and configured to either change or maintain the pH in the sample solution. Such an automatic method of pH modulation may be applied to analyzing immunoassays and other bioassays which may involve biomarkers that have soluble binding partners.

Aspects of the present disclosure are directed to methods for detecting an amount of an analyte in a solution using an electrochemical pH modulation technology. The solution may include soluble binding partners of the analyte, which may bind to analytes in the solution to form complexes. The soluble binding partners may be drugs in the solution. The solution may also include detecting probes configured to bind to the analytes in the solution for detecting the amount of the analyte in the solution. Each detecting probe may include a signaling tag attached thereto. In one embodiment, aspects of the present disclosure include an acid pre-treatment step where analytes, such as anti-drug antibodies (ADAs), may be dissociated from their binding partners, followed by binding to capture molecules and to detecting probes for detecting an amount of an analyte in a solution. In another embodiment, aspects of the present disclosure include an acid pre-treatment step where analytes, such as ADAs, may be dissociated from their binding partners, followed by electrochemically modulating (e.g. neutralizing) a pH of a solution to allow the analytes to bind to capture molecules and to detecting probes for detecting an amount of an analyte in the solution. In yet another embodiment, aspects of the present disclosure utilize detecting probes having pH-dependent signaling tags attached thereto for detecting an amount of an analyte, such as an ADA, in a solution, where a pH-dependent signaling tag may produce a first signal when the solution is at a first pH value, and may produce a second signal when the solution is at a second pH value different from the first pH value.

FIG. 1 depicts a schematic diagram of a method for detecting an amount of an analyte in an assay. The assay may be a bridging ELISA assay. The analyte may be an ADA. As shown in FIG. 1, a capture molecule 10 is attached to a solid substrate 12 (e.g. an electrode) via a linker 14. An analyte 16 may bind to the capture molecule 10. A detecting probe 18 may be present in the assay and may include a signaling tag 20 attached thereto. As illustrated in FIG. 1, the detecting probe 18 may bind to the analyte 16, and the signaling tag 20 may produce a signal. Thereafter, the amount of the analyte 16 in the assay may be calculated based on the signal.

The linker 14 is configured to immobilize the capture molecule 10 and to preserve the functionality thereof. Specifically, the linker 14 may be a polymeric material configured to immobilize the capture molecule through adsorption. The polymeric material may be, but not limited to, polystyrene, polymethyl methacrylate (PMMA), polypropylene, cyclic olefin copolymer, agarose, dextran, or nitrocellulose. The linker may also be a peptide sequence or a protein configured to immobilize the capture molecule through affinity. The peptide sequence or the protein may be, but not limited to, streptavidin, protein A, or protein G, an aptamer, or a polyhistidine tag (His-Tag). In addition, the linker may be a polynucleic acid configured to immobilize the capture molecule through hybridization. Further, the linker may be an organic molecule for immobilizing the capture molecule through covalent bonding. The organic molecule may be, but not limited to, maleimide, succinimide, (trifluoromethyl)

phenyldiaziridine, amine, hydrazide, boronic acid, iodo-acetyl, epoxide, thiol, azide, or alkyne.

The signaling tag 20 may be pH-dependent or pH-independent. Basically, a pH-dependent signaling tag may change its behavior as a function of a pH of a solution. For example, a pH-dependent signaling tag may produce a first signal at a first pH value and may produce a second signal at a second pH value, where the first and the second pH value are different. On the contrary, a pH-independent signaling tag may not change its behavior as a function of a pH of a solution, but rather produce a signal when it presents in a solution.

As to compositions, the signaling tag 20 may be a fluorescent tag, a fluorescent dye, a fluorescent protein, an electroluminescent dye, a chemiluminescent dye, or an enzyme.

Specifically, fluorescent tags can be pH-dependent or pH-independent, which may be, but not limited to, organic dyes, quantum dots, lanthanide ions, or proteins. Fluorescent dyes may be, but not limited to, fluorescein, coumarin, rhodamin, cyanine, or derivatives thereof. Examples of commonly used fluorescent dyes include fluorescein isothiocyanate (FITC), tetramethylrhodamine isothiocyanate (TRITC), Alexa Fluor, Cy-3, Cy-5, and ATTO dyes. Examples of pH-dependent fluorescent dyes may include, but not limited to, pHrodo, Protonex, Oregon Green, LysoSensor Green, pHAb, fluorescein, FAM, rhodamine B derivatives, and SNARF. In addition, fluorescent proteins can be pH-dependent or pH-independent, which may be, but not limited to, green fluorescent proteins, yellow fluorescent proteins, or cyan fluorescent proteins. Further, electroluminescent dyes may be fluolid dyes, such as Fluolid-Green, Fluolid-Orange, and Fluolid-Red. Chemiluminescent dyes may be, but not limited to, luminol, luciferin, or xanthene dyes. Examples of pH-dependent enzymes include horseradish peroxidase (HRP), glucose oxidase, and alkaline phosphatase.

Referring to FIG. 1, the signal produced by the signaling tag 20 may be an optical signal, an electronic signal, or a chemical signal. Particularly, the optical signal may be in a form of, but not limited to, fluorescence, colorimetry, turbidometry, chemiluminescence, or electroluminescence. Further, the chemical signal may be in a form of, but not limited to, radiation, or a pH change.

Figure 2:
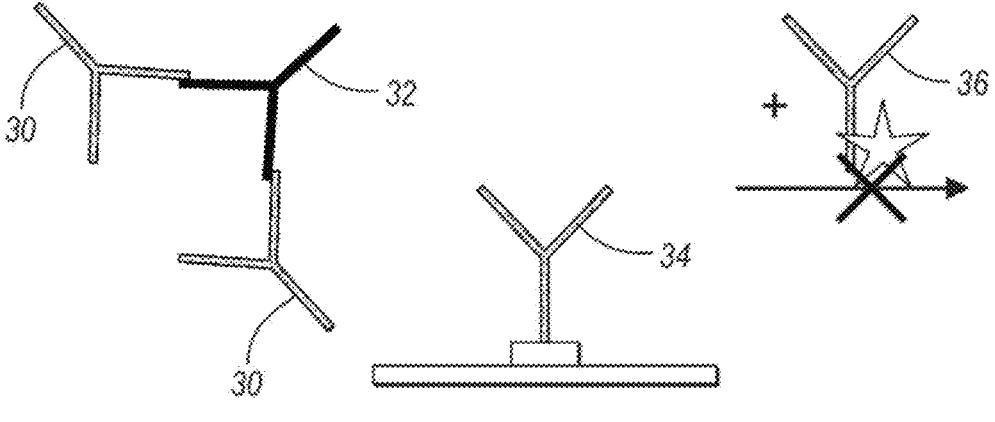
FIG. 2 depicts a schematic diagram illustrating an interference of the presence of soluble binding partners of an analyte with the detection of an amount of the analyte in an assay.

FIG. 2 depicts a schematic diagram illustrating an interference of the presence of soluble binding partners of an analyte with the detection of an amount of the analyte in an assay. The assay may be a bridging ELISA assay. The analyte may be an ADA. The soluble binding partners may be drugs in the assay. As illustrated in FIG. 2, binding partners 30 in the assay may bind to an analyte 32, thereby forming a complex which may prevent the analyte 32 from binding to a capture molecule 34 or even to a detecting probe 36. The formation of the complex may thus affect the accuracy of the detection of the amount of the analyte in the assay.

Figure 3:
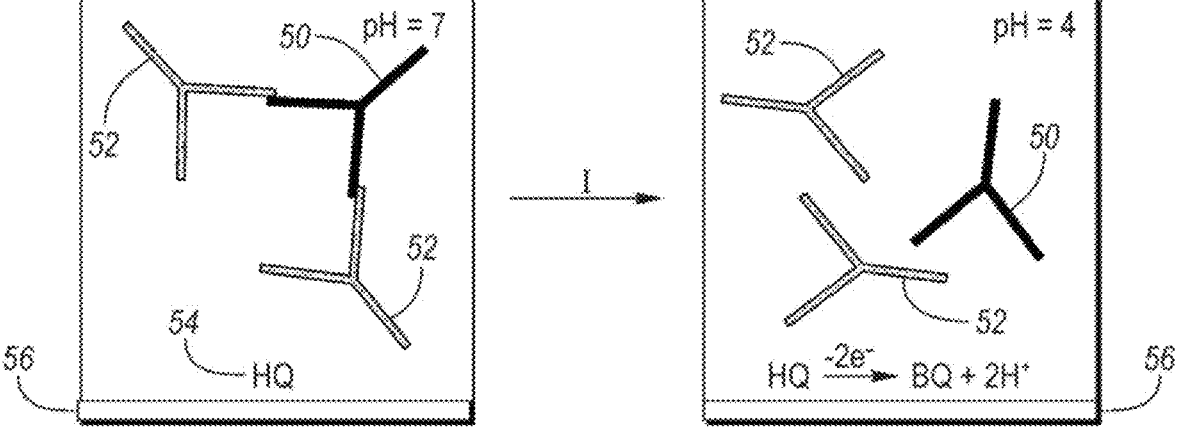
FIG. 3 depicts a schematic diagram illustrating an acid pre-treatment step to dissociate analytes from soluble binding partners of the analytes in an assay.

FIG. 3 depicts a schematic diagram illustrating an acid pre-treatment step to dissociate analytes from soluble binding partners of the analytes in an assay. The assay may be a bridging ELISA assay. The analyte may be an ADA. The soluble binding partners may be drugs in the assay. As described in FIG. 2, soluble binding partners may bind to analytes, thereby forming complexes in the assay. Similarly, as shown in FIG. 3, the formation of such a complex occurs when a pH of a solution in the assay is 7, where soluble binding partners 52 bind to the analyte 50. To dissociate the analyte 50 from the bounded binding partners 52, electrochemically active agents, such as hydroquinone (HQ) 54, may be added into the solution. The electrochemically active agents may either generate or consume hydrogen (H⁺) ions in the solution through an electrochemical redox reaction (i.e. oxidation or reduction), which accordingly modifies the pH of the solution.

Referring to FIG. 3, the solution may include both HQ 54 and benzoquinone (BQ) (not shown). Controlling an electrical current applied to an electrode in contact with the solution may either induce an oxidization reaction of HQ 54 or a reduction reaction of BQ, thus either generating H⁺ ions or consuming H⁺ ions in the solution, respectively.

FIG. 3 illustrates a scenario where HQ 54 is oxidized under the influence of the electrical current (I) applied to the electrode 56, generating BQ and H⁺ ions in the solution.

$$HQ \rightarrow BQ + 2H^+ + 2e^- \qquad (1)$$

The oxidization reaction of HQ may thus modify the pH of the solution, especially an area in the solution that is close to the electrode 56, from pH 7 to pH 4. Incubating the solution at pH 4 may allow the analyte 50 to be dissociated from the binding partners 52.

Other electrochemically active agents may also be utilized for electrochemically modulating a pH of a solution, such as quinone, catechol, aminophenol, hydrazine, naphthoquinone, derivatives thereof, or combinations thereof. Each of the electrochemically active agents may undergo an electrochemical redox reaction (i.e. oxidation or reduction) under the influence of an electrical current, which may either generate or consume H⁺ ions in the solution for modulating the pH of the solution.

Figure 4:
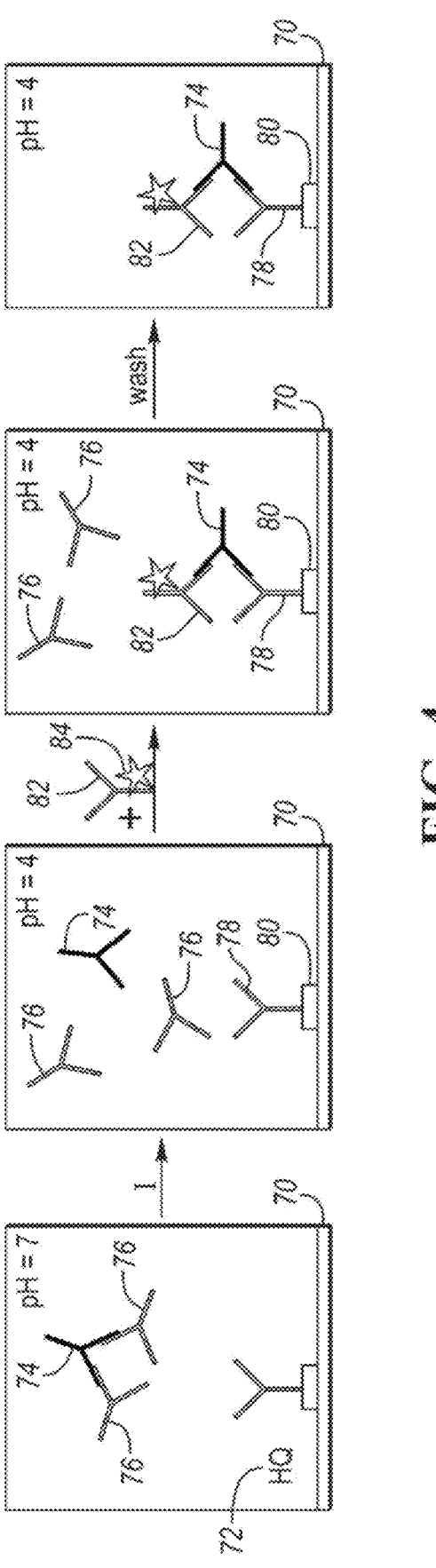
FIG. 4 depicts a schematic diagram illustrating a first method embodiment for detecting an amount of an analyte in an assay.

FIG. 4 depicts a schematic diagram illustrating a first method embodiment for detecting an amount of an analyte in an assay. The assay may be a bridging ELISA assay. The analyte may be an ADA. As described in FIG. 3, an acid pre-treatment step may be performed to dissociate analytes from their soluble binding partners (e.g. drugs) bound to the analytes through electrochemically modulating a pH of a solution. The solution may include both HQ and BQ. Similarly, as shown in FIG. 4, upon applying an electrical current (I) to an electrode 70 in contact with the solution, an electrochemically active agent 72, such as HQ, may be oxidized. The oxidation of HQ generates H⁺ ions in the solution, which induces a pH change of the solution from pH 7 to pH 4. Incubating the solution at pH 4 may allow the analyte 74 to be dissociated from the binding partners 76 and to bind to a capture molecule 78. The capture molecule 78 may be attached to the electrode 70 via a linker 80. The linker 80 is configured to immobilize the capture molecule 78 through adsorption, affinity, hybridization, or covalent bonding.

To accurately measure the amount of the analyte 74 in the assay, an excess amount of detecting probes 82 may be added to the solution at pH 4. Each detecting probe 82 may have a signaling tag 84 attached thereto and configured to produce a signal at pH 4. As shown in FIG. 4, the analyte 74 may bind to a detecting probe 82 at pH 4. Upon the completion of binding at pH 4, a wash step may be performed to remove any unbound detecting probes 82 in the solution. The method may then measure the signals produced by the signaling tags 84 remained in the solution and calculate the amount of the analyte 74 in the assay based on the signals.

Figure 5:
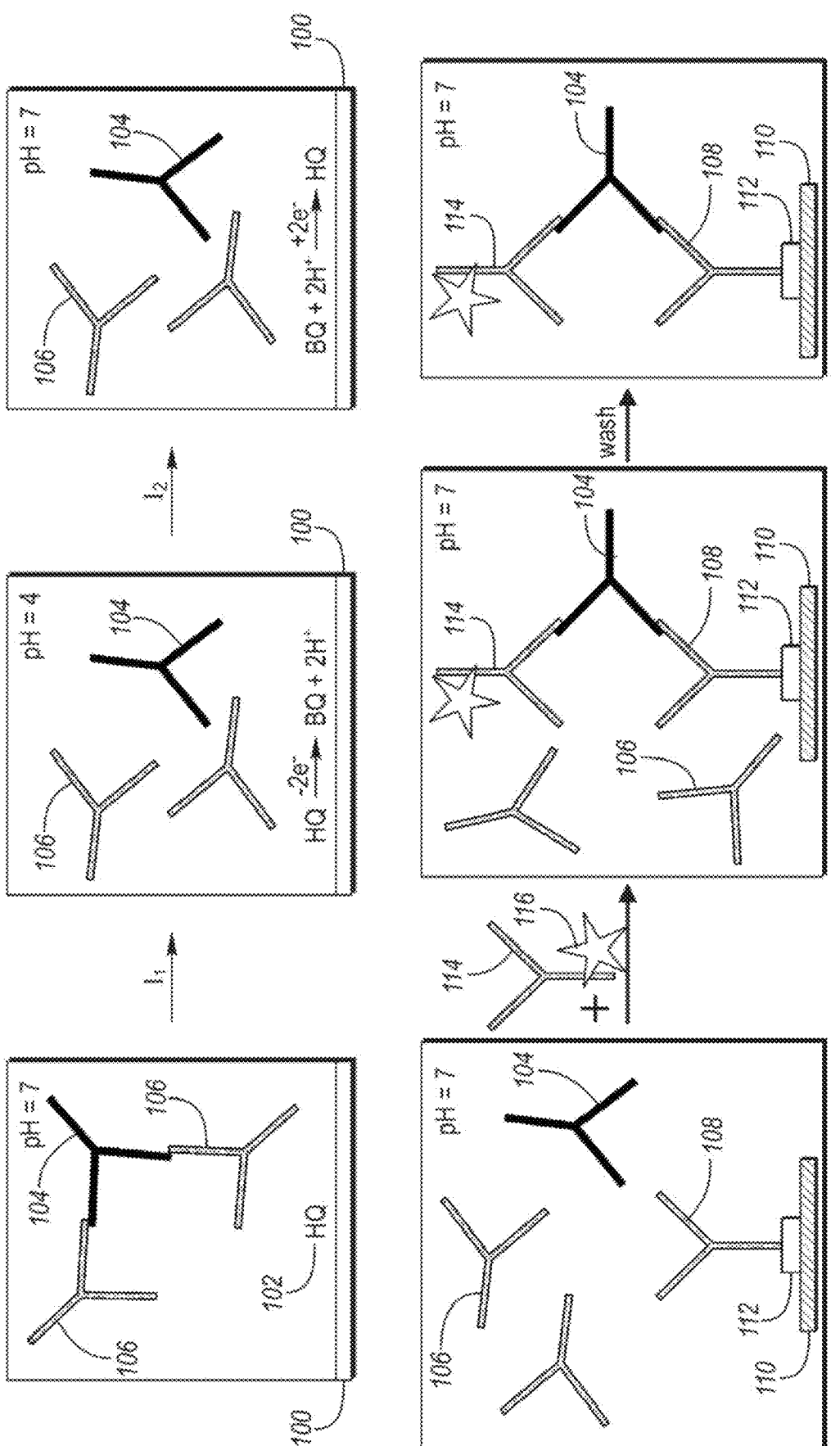
FIG. 5 depicts a schematic diagram illustrating a second method embodiment for detecting an amount of an analyte in an assay.

FIG. 5 depicts a schematic diagram illustrating a second method embodiment for detecting an amount of an analyte in an assay. The assay may be a bridging ELISA assay. The analyte may be an ADA. As both described in FIGS. 3 and 4, an acid pre-treatment step may be performed to dissociate analytes from their soluble binding partners (e.g. drugs) bound to the analytes through electrochemically modulating a pH of a solution. The solution may include both HQ and BQ. Therefore, as shown in FIG. 5, at pH 7, upon applying a first electrical current ($I_1$) to an electrode 100 in contact with a solution, an electrochemically active agent 102, such as HQ, may be oxidized. The oxidation of HQ generates $H^+$ ions in the solution, which induces a pH change of the solution from pH 7 to pH 4. Incubating the solution at pH 4 may allow the analyte 104 to be dissociated from the binding partners 106.

To afford optimal bindings between the analyte 104 and a capture molecule 108 in the assay, and between the analyte 104 and a detecting probe 110, the pH of the solution may be further adjusted. As shown in FIG. 5, upon applying a second electrical current ($I_2$) to the electrode 100, BQ in the solution may be reduced. The reduction of BQ consumes $H^+$ ions in the solution, which induces a pH change of the solution from pH 4 to pH 7.

$$BQ+2H^++2e^-\rightarrow HQ \quad (2)$$

Thereafter, the solution may be transferred to an assay chamber, where the analyte 104 may bind to the capture molecule 108. The capture molecule 108 may be attached to a solid substrate 110 in the assay chamber via a linker 112. The linker 112 is configured to immobilize the capture molecule 108 through adsorption, affinity, hybridization, or covalent bonding.

To accurately measure the amount of the analyte 104 in the assay, an excess amount of detecting probes 114 may be added to the solution at pH 7. Each detecting probe 114 may have a signaling tag 116 attached thereto and configured to produce a signal at pH 7. As shown in FIG. 5, the analyte 104 may bind to the detecting probe 114 at pH 7. Upon completion of binding at pH 7, a wash step may be performed to remove any unbound detecting probes 114 in the solution. The method may then measure the signals produced by the signaling tags 116 remained in the solution and calculate the amount of the analyte 104 in the assay based on the signals.

Figure 6:
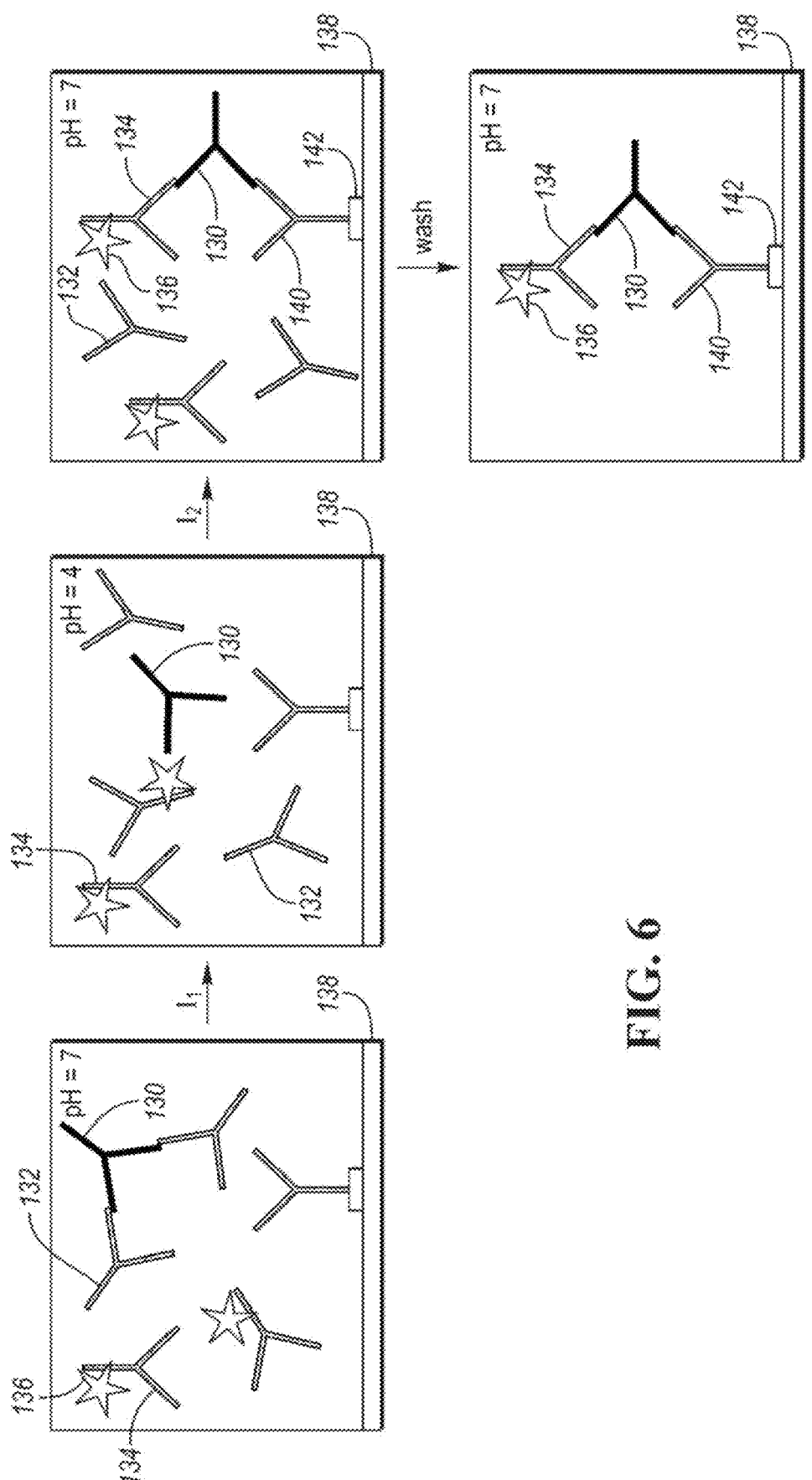
FIG. 6 depicts a schematic diagram illustrating a third method embodiment for detecting an amount of an analyte in an assay.

FIG. 6 depicts a schematic diagram illustrating a third method embodiment for detecting an amount of an analyte in an assay. The assay may be a bridging ELISA assay. The analyte may be an ADA. The method may be a one-pot immunoassay format for the detection of an amount of an analyte in the immunoassay. As shown in FIG. 6, a pH of a solution in an assay chamber is 7, where an analyte 130 is bound by its binding partners 132 in the solution. The binding partners may be drugs in the assay. At pH 7, the assay chamber may also include detecting probes 134 which may have been added to the solution. Each detecting probe 134 may have a signaling tag 136 attached thereto and configured to produce a signal. As discussed above, an acid pre-treatment step may be performed to dissociate analytes from their soluble binding partners (e.g. drugs) bound to the analytes through electrochemically modulating a pH of a solution. The solution may include both HQ and BQ. Therefore, as shown in FIG. 6, upon applying a first electrical current ($I_1$) to an electrode 138 in contact with the solution, an electrochemically active agent (not shown), such as HQ, may be oxidized. The oxidation of the electrochemically active agent generates $H^+$ ions in the solution, which modulates the pH of the solution from pH 7 to pH 4. Incubating the solution at pH 4 may allow the analyte 130 to be dissociated from the binding partners 132.

To achieve optimal bindings between the analyte 130 and a capture molecule 140 in the assay, and between the analyte 130 and a detecting probe 134, the pH of the solution may be further adjusted. As shown in FIG. 6, applying a second electrical current ($I_2$) to the electrode 138 may reduce another electrochemically active agent (not shown), such as BQ, in the solution. The reduction reaction consumes $H^+$ ions in the solution, which induces a pH change of the solution from pH 4 to pH 7. At pH 7, the analyte 130 may bind to the capture molecule 140. The capture molecule may be attached to the electrode 138 via a linker 142. The linker 142 is configured to immobilize the capture molecule 140 through adsorption, affinity, hybridization, or covalent bonding. Further, the analyte 130 may bind to the detecting probe 134 in the solution at pH 7.

In one embodiment, the signaling tag 136 may be pH-independent, where the signaling tag 136 may produce the same signal when the pH of the solution is at either 4 or 7. In this case, upon the completion of binding at pH 7, a wash step may be performed to remove any unbound detecting probes 134 in the solution. The method may then measure the signals produced by the signaling tags 136 remained in the solution and calculate the amount of the analyte 130 in the assay based on the signals.

In another embodiment, the signaling tag 136 may be pH-dependent, where the signaling tag 136 may produce a first signal at pH 4 and may produce a second signal at pH 7, the second signal being different from the first signal. In this embodiment, an optimal pH for the signaling tag 136 to produce a signal is 7. In other words, the second signal produced at pH 7 may be stronger than the first signal produced at pH 4. In this case, upon the completion of binding at pH 7, a wash step may be performed to remove any unbound detecting probes 134 in the solution. The method may then measure the second signal produced by the signaling tags 136 remained in the solution and calculate the amount of the analyte 130 in the assay based on the second signal.

Figure 7:
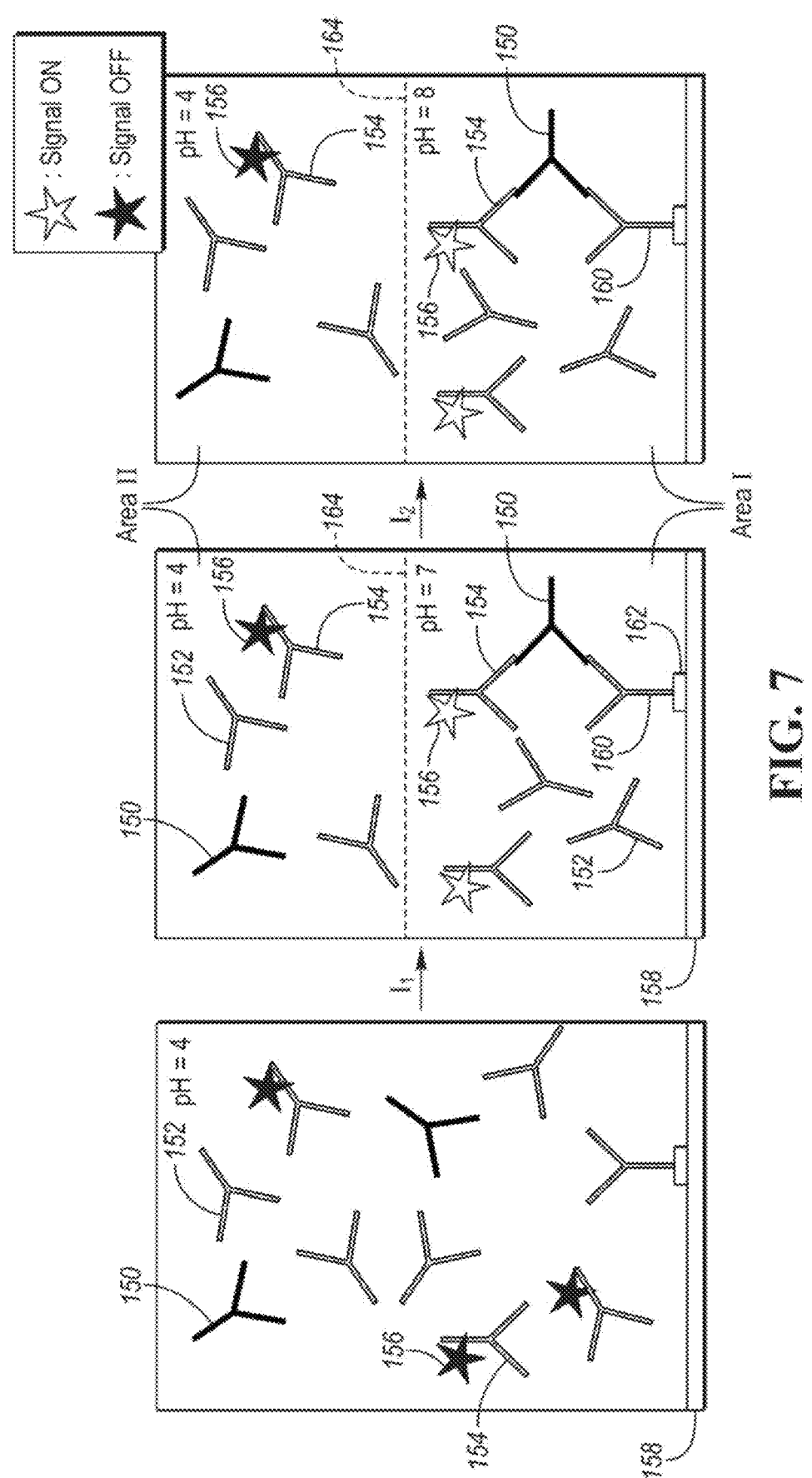
FIG. 7 depicts a schematic diagram illustrating a fourth method embodiment for detecting an amount of an analyte in an assay.

FIG. 7 depicts a schematic diagram illustrating a fourth method embodiment for detecting an amount of an analyte in an assay. The assay may be a bridging ELISA assay. The analyte may be an ADA. The method may be a single-step immunoassay format for the detection of an amount of an analyte in the immunoassay. As shown in FIG. 7, an assay chamber contains a solution of pH 4, where analytes 150 are not bound by their binding partners 152 in the solution. The binding partners 152 may be drugs in the assay chamber. The assay chamber may also include detecting probes 154. Each detecting probe 154 may have a signaling tag 156 attached thereto. The signaling tag 156 may be pH-dependent in this method embodiment. As illustrated in FIG. 7, the signaling tag 156 may not produce a signal (i.e. signal OFF) at pH 4.

As discussed above, under the influence of an electrical current applied to an electrode in contact with a solution, electrochemically active agents can subsequently modulate a pH of the solution in an automatic manner. The solution may include both HQ and BQ. Therefore, referring to FIG. 7, by applying a first electrical current ($I_1$) to an electrode 158 in contact with a solution in the assay chamber, a first electrochemically active agent (not shown) may be reduced, thereby consuming $H^+$ ions in the solution. In this method embodiment, by controlling the $I_1$ applied to the electrode 158, only the solution near a surface of the electrode 158 may undergo a pH change, while the pH of other areas of the solution may not be changed. Specifically, as shown in FIG. 7, the reduction reaction of the first electrochemically active agent may induce a pH change from pH 4 to pH 7 near the surface of the electrode 158, Area I (i.e. below a modulation line 164), whereas other areas of the solution, Area II (i.e. above the modulation line 164), may remain at pH 4. Accordingly, in Area II, at pH 4, the signaling tags 156 may still not produce signals (i.e. signal OFF). On the other hand, in Area I, at pH 7, an analyte 150 may bind to a capture molecule 160. The capture molecule 160 may be attached to the electrode 158 via a linker 162. The linker 162 is configured to immobilize the capture molecule 160 through adsorption, affinity, hybridization, or covalent bonding. In addition, in Area I, at pH 7, the analyte 150 may bind to a detecting probe 154, and the signaling tag 156 attached to the detecting probe 154 may produce a first signal.

In this method embodiment, an optimal pH for the analyte 150 to bind to the capture molecule 160 and to the detecting probe 154 may be 7. However, an optimal pH for the signaling tag 156 to produce a signal may be, for example, 8. Therefore, as shown in FIG. 7, to obtain a stronger detecting signal produced by the signaling tag 156, the method may further slightly adjust the pH of the solution from 7 to 8 by applying a second electrical current ($I_2$) to the electrode 158. Similarly, by controlling the $I_2$ applied to the electrode 158, only the solution near the surface of the electrode 158, Area I, may undergo the pH change, whereas other areas of the solution, Area II, may remain at pH 4. Accordingly, in Area II, at pH 4, the signaling tags 156 may still not produce signals (i.e. signal OFF). On the other hand, in Area I, at pH 8, the analyte 150 may still bind to the capture molecule 160 and to the detecting probe 154. In addition, in Area I, at pH 8, the signaling tag 156 attached to the detecting probe 154 may produce a second signal. Since the signaling tag 156 is pH-dependent, and the optimal pH for the signaling tag 156 to produce a signal is 8, the second signal may be, therefore, stronger than the first signal produced at pH 7. As such, the amount of the analyte 150 in the assay chamber may be accurately calculated based on the second signal.

Figure 8:
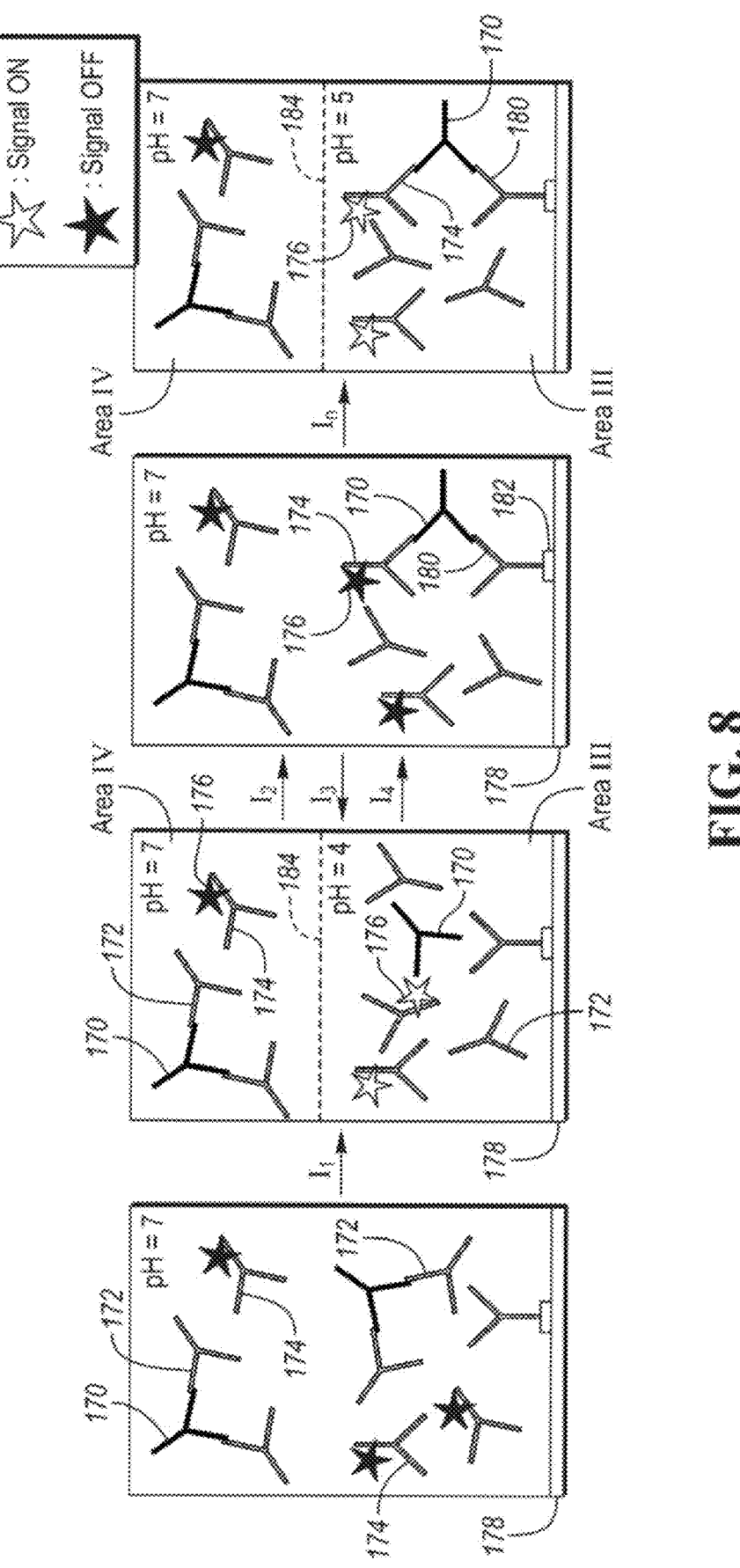
FIG. 8 depicts a schematic diagram illustrating a fifth method embodiment for detecting an amount of an analyte in an assay.

FIG. 8 depicts a schematic diagram illustrating a fifth method embodiment for detecting an amount of an analyte in an assay. The assay may be a bridging ELISA assay. The analyte may be an ADA. The method may be a single-step immunoassay format for the detection of an amount of an analyte in the immunoassay. As shown in FIG. 8, a pH of a solution in an assay chamber is 7, where analytes 170 are bound by their binding partners 172 in the solution. The binding partners 172 may be drugs in the assay chamber. At pH 7, the assay chamber may also include detecting probes 174. Each detecting probe 174 may have a signaling tag 176 attached thereto. The signaling tag 176 may be pH-dependent in this method embodiment. As illustrated in FIG. 8, the signaling tag 176 may not produce a signal (i.e. signal OFF) at pH 7.

Similar to FIG. 7, in FIG. 8, applying a first electrical current ($I_1$) to an electrode 178 in contact with the solution in the assay chamber may oxidize a first electrochemically active agent (not shown) in the solution, and the oxidization reaction of the first electrochemically active agent may induce a pH change of the solution. In addition, by controlling the $I_1$ applied to the electrode 178, only the solution near a surface of the electrode 178, Area III (i.e. below a modulation line 184), may undergo the pH change from pH 7 to pH 4, whereas the pH of other areas in the solution, Area IV (i.e. above the modulation line 184), may not be changed (i.e. remain at pH 7). Accordingly, in Area IV, at pH 7, the analyte 170 may still be bound by its binding partners 172, and the signaling tag 176 may still not produce a signal. On the other hand, in Area III, the analyte 170 may be dissociated from its binding partners 172, and the signaling tag 176 may produce a signal (i.e. signal ON).

Thereafter, applying a second electrical current ($I_2$) to the electrode 178 may trigger a second electrochemically active agent (not shown) in the solution to undergo a reduction reaction, thereby changing the pH of the solution at Area III back to pH 7. At this stage, both areas of the solution, Area III and Area IV, are at pH 7, and an analyte 170 may bind to a capture molecule 180 in the assay chamber. The capture molecule 180 may be attached to the electrode 178 via a linker 182. The linker 182 is configured to immobilize the capture molecule 160 through adsorption, affinity, hybridization, or covalent bonding. However, as shown in FIG. 8, at pH 7, the signaling tag 176 may not produce a signal (i.e. signal OFF) even though the detecting probe 174 may bind to the analyte 170.

To ensure as much as analytes 170 in the solution to be dissociated from their binding partners 172, a third electrical current ($I_3$) may then be applied to the electrode 178 to initiate an oxidation reaction of a third electrochemically active agent (not shown) in the solution. The oxidation reaction may reduce the pH of the solution back to pH 4, especially the solution in Area III that is near to the surface of the electrode 178. Incubating the solution at pH 4 can afford more analytes 170 to be dissociated from the binding partners 172. Thereafter, applying a fourth electrical current ($I_4$) may once again bring the pH of the solution back to pH 7. Such a process of oxidation and reduction reactions of electrochemically active agents may repeat several times to maximize the number of analytes 170 that are not bound by binding partners 172 in the solution such that the analytes 170 are available to be detected by the detecting probes 174.

Referring to FIG. 8, the signaling tag 176 is pH-dependent, and an optimal pH for the signaling tag 176 to produce a signal may be, for example, 5. Therefore, as shown in FIG. 8, applying another electrical current ($I_n$) to the electrode 178 may further trigger another electrochemically active agent in the solution to undergo another oxidation reaction such that the pH of the solution, especially Area III, may further be modulated from 7 to 5. At pH 5, the analyte 170 may still bind to the capture molecule 180 and to the detecting probe 174. In addition, the signaling tag 176 may produce a signal at pH 5. As such, the amount of the analyte 170 in the assay chamber may be accurately calculated based on the signal produced at pH 5.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method for detecting an amount of an analyte in a solution comprising:

providing an assay chamber including an electrode positioned at the assay chamber and a capture molecule attached to the electrode via a linker;

providing to the assay chamber a solution including an analyte, a binding partner of the analyte, at least one electrochemically active agent, and a detecting probe having a pH-dependent signaling tag attached thereto, the solution is in contact with the electrode and has a first pH value at which the pH-dependent signaling tag does not produce a signal and the analyte is not bound to the binding partner of the analyte;

applying a first electrical signal to the electrode to change the pH of the solution near the surface of the electrode from the first pH value to a second pH value, while the pH of other areas of the solution remains at the first pH value;

binding the analyte to the capture molecule and to the detecting probe at the first end of the assay chamber; and measuring a signal produced by the pH-dependent signaling tag at the second pH value near the surface of the electrode, wherein the pH-dependent signaling tag in the other areas of the solution at the first pH value does not produce a signal.

2. The method of claim 1, wherein the second pH value is higher than the first pH value.

3. The method of claim 1, wherein the analyte is an anti-drug antibody (ADA).

4. The method of claim 1, wherein the electrochemically active agent is selected from the group consisting of quinone, catechol, aminophenol, hydrazine, hydroquinone, benzoquinone, naphthoquinone, derivatives thereof, and combinations thereof.

5. The method of claim 1, wherein the signaling tag is selected from the group consisting of a fluorescent tag, a fluorescent dye, a fluorescent protein, an electroluminescent dye, a chemiluminescent dye, and an enzyme.

6. A method for detecting an amount of an analyte in a solution comprising:

providing an assay chamber including an electrode positioned at the assay chamber and a capture molecule attached to the electrode via a linker;

providing to the assay chamber a solution including an analyte, a binding partner of the analyte, at least one electrochemically active agent, and a detecting probe having a pH-dependent signaling tag attached thereto, the solution is in contact with the electrode and has a first pH value at which the pH-dependent signaling tag does not produce a signal and the analyte is not bound to the binding partner of the analyte;

applying a first electrical signal to the electrode to change the pH of the solution near the surface of the electrode from the first pH value to a second pH value, while the pH of other areas of the solution remains at the first pH value;

binding the analyte to the capture molecule and to the detecting probe at the first end of the assay chamber, wherein the pH-dependent signaling tag near the surface of the electrode produces a first signal at the second pH value and wherein the pH-dependent signaling tag in the other areas of the solution at the first pH value does not produce a signal;

applying a second electrical signal to the electrode to change the pH of the solution near the surface of the electrode from the second pH value to a third pH value, while the pH of other areas of the solution remains at the first pH value; and measuring a second signal produced by the pH-dependent signaling tag at the third pH value near the surface of the electrode, wherein the pH-dependent signaling tag in the other areas of the solution at the first pH value does not produce a signal.

7. The method of claim 6, wherein the second pH value is higher than the first pH value.

8. The method of claim 6, wherein the third pH value is higher than the second pH value.

9. The method of claim 6, wherein the analyte is an anti-drug antibody (ADA).

10. The method of claim 6, wherein the electrochemically active agent is selected from the group consisting of quinone, catechol, aminophenol, hydrazine, hydroquinone, benzoquinone, naphthoquinone, derivatives thereof, and combinations thereof.

11. The method of claim 6, wherein the signaling tag is selected from the group consisting of a fluorescent tag, a fluorescent dye, a fluorescent protein, an electroluminescent dye, a chemiluminescent dye, and an enzyme.

12. A method for detecting an amount of an analyte in a solution comprising:

providing an assay chamber including an electrode positioned at the assay chamber and a capture molecule attached to the electrode via a linker;

providing to the assay chamber a solution including an analyte, a binding partner of the analyte, at least one electrochemically active agent, and a detecting probe having a pH-dependent signaling tag attached thereto, the solution is in contact with the electrode and has a first pH value at which the pH-dependent signaling tag does not produce a signal and the analyte is bound to the binding partner of the analyte;

applying a first electrical signal to the electrode to change the pH of the solution near the surface of the electrode from the first pH value to a second pH value, while the pH of other areas of the solution remains at the first pH value;

dissociating the binding partner of the analyte from the analyte at the first end of the assay chamber at the second pH value;

applying a second electrical signal to the electrode to change the pH of the solution near the surface of the electrode from the second pH value to the first pH value, while the pH of other areas of the solution are at the first pH value;

binding the analyte to the capture molecule and to the detecting probe at the first end of the assay chamber;

applying a third electrical signal to the electrode to change the pH of the solution near the surface of the electrode from the first pH value to the second pH value, while the pH of other areas of the solution remains at the first pH value;

dissociating the binding partner of the analyte from the analyte at the first end of the assay chamber at the second pH value;

applying a fourth electrical signal to the electrode to change the pH of the solution near the surface of the electrode from the second pH value to the first pH value, while the pH of other areas of the solution are at the first pH value;

binding the analyte to the capture molecule and to the detecting probe at the first end of the assay chamber;

applying a next electrical signal to the electrode to change the pH of the solution at the first end of the assay chamber from the second pH value to a third pH value, the pH-dependent signaling tag is in an on state at the third pH value; and measuring a signal produced by the pH-dependent signaling tag at the third pH value.

13. The method of claim 12, further comprising shifting the pH of the solution in the first end of the assay chamber between the first and second pH values prior to applying the next electrical signal to the electrode to change the pH of the solution at the first end of the assay chamber from the second pH value to the third pH value.

14. The method of claim 12, wherein the second pH value is lower than the first pH value.

15. The method of claim 12, wherein the third pH value is higher than the second pH value.

16. The method of claim 12, wherein the analyte is an anti-drug antibody (ADA).

17. The method of claim 12, wherein the electrochemically active agent is selected from the group consisting of quinone, catechol, aminophenol, hydrazine, hydroquinone, benzoquinone, naphthoquinone, derivatives thereof, and combinations thereof.

18. The method of claim 12, wherein the signaling tag is selected from the group consisting of a fluorescent tag, a fluorescent dye, a fluorescent protein, an electroluminescent dye, a chemiluminescent dye, and an enzyme.

19. The method of claim 12, wherein the linker is configured to immobilize the capture molecule through adsorption.

20. The method of claim 12, wherein the linker is configured to immobilize the capture molecule through covalent bonding.

* * * * *